(12) United States Patent
Wong et al.

(10) Patent No.: US 8,768,025 B2
(45) Date of Patent: Jul. 1, 2014

(54) DENTAL SHADE MAPPING

(71) Applicant: Carestream Health, Inc., Rochester, NY (US)

(72) Inventors: Victor C. Wong, Rochester, NY (US); James R. Milch, Penfield, NY (US); Lawrence A. Ray, Rochester, NY (US); Peter D. Burns, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 14/040,776

(22) Filed: Sep. 30, 2013

(65) Prior Publication Data
US 2014/0030670 A1 Jan. 30, 2014

Related U.S. Application Data

(62) Division of application No. 12/834,921, filed on Jul. 13, 2010, now Pat. No. 8,571,281.

(51) Int. Cl.
*G06K 9/00* (2006.01)

(52) U.S. Cl.
USPC .............. 382/128; 382/162; 382/294; 433/29

(58) Field of Classification Search
USPC ...................... 382/128, 162–167, 294; 433/29
See application file for complete search history.

(56) References Cited

U.S. PATENT DOCUMENTS

| | | | |
|---|---|---|---|
| 4,836,674 A | 6/1989 | Lequime et al. | |
| 5,383,020 A | 1/1995 | Vieillefosse | |
| 5,745,229 A | 4/1998 | Jung et al. | |
| 5,766,006 A | 6/1998 | Murljacic | |
| 6,008,905 A | 12/1999 | Breton et al. | |
| 6,038,024 A | 3/2000 | Berner | |
| 6,867,864 B2 | 3/2005 | Overbeck et al. | |
| 7,064,830 B2 | 6/2006 | Giorgianni et al. | |
| 7,570,984 B2 * | 8/2009 | Katsuda et al. | 600/407 |

(Continued)

FOREIGN PATENT DOCUMENTS

| | | |
|---|---|---|
| EP | 1 566 617 | 8/2005 |
| WO | WO 2005/080929 | 9/2005 |

OTHER PUBLICATIONS

Peter D. Burns and Roy S. Berns, "Analysis Multispectral Image Capture", *Fourth Color Imaging Conference: Color Science Systems and Applications*, 1996, pp. 19-22.

(Continued)

*Primary Examiner* — Wesley Tucker

(57) ABSTRACT

A method and apparatus for generating a color mapping for a dental object. The method includes generating a transformation matrix according to a set of spectral reflectance data for a statistically valid sampling of teeth. Illumination is directed toward the dental object over at least a first, a second, and a third wavelength band, one wavelength band at a time. For each of a plurality of pixels in an imaging array, an image data value is obtained, corresponding to each of the at least first, second, and third wavelength bands. The transformation matrix is applied to form the color mapping by generating a set of visual color values for each of the plurality of pixels according to the obtained image data values and according to image data values obtained from a reference object at the at least first, second, and third wavelength bands. The color mapping can be stored in an electronic memory.

4 Claims, 13 Drawing Sheets

(56) References Cited

U.S. PATENT DOCUMENTS

| | | | |
|---|---|---|---|
| 7,668,355 B2* | 2/2010 | Wong et al. | 382/128 |
| 2007/0140553 A1* | 6/2007 | Katsumata | 382/162 |
| 2008/0118886 A1* | 5/2008 | Liang et al. | 433/29 |
| 2009/0131800 A1* | 5/2009 | Liang | 600/476 |
| 2009/0274998 A1* | 11/2009 | Wong et al. | 433/215 |
| 2012/0014571 A1* | 1/2012 | Wong et al. | 382/128 |
| 2012/0014572 A1* | 1/2012 | Wong et al. | 382/128 |

OTHER PUBLICATIONS

Peter D. Burns, Analysis of Image Noise in Multispectral Color Acquisition, dissertation, Center for Imaging, Rochester Institute of Technology, May 1997, 194 pages.

European Search Report, dated Oct. 21, 2011 for European Patent Application No. 11005518.3, 2 pages.

* cited by examiner

DENTAL SHADE MAPPING

CROSS REFERENCE TO RELATED APPLICATIONS

This application is a Divisional of U.S. Ser. No. 12/834,921 filed on Jul. 13, 2010 entitled "DENTAL SHADE MAPPING", in the names of Wong et al, incorporated herein in its entirety.

FIELD OF THE INVENTION

This invention relates generally to methods and systems for dental color measurement and more particularly relates to a digital method and system for determining color shade information for natural teeth, reference shade samples, and fabricated dental prostheses.

BACKGROUND OF THE INVENTION

Modern restorative dental procedures often require accurate color matching, such as for filling materials and for the fabrication of restorations such as crowns, implants, fixed partial dentures, and veneers. The materials used for these procedures, such as ceramics and other materials, can be skillfully formed and treated to closely match the shape, texture, color and translucency of natural teeth.

A widely used technique for determining and communicating tooth color information is a process referred to as "shade matching" whereby the dentist or technician visually matches a patient's tooth to one of a number of reference shade samples or shade tabs within one or more sets of standardized shade guides. The practitioner who performs the match records the identification of the matching shade tab and conveys that information to the dental laboratory where the restoration or prosthesis is then fabricated. The laboratory then uses its own set of the same shade guides to perform visual color evaluations of the restoration or prosthesis throughout the fabrication process.

The visual shade matching process can be highly subjective and subject to a number of problems. The initial matching procedure is often difficult and tedious, and it is not unusual for the process to take twenty minutes or longer. In many cases, there is no shade tab that perfectly matches the patient's teeth.

The problem of accurately modeling the color of a tooth is more complex than obtaining a close color match using shade tabs. The inherent shortcomings and limitations of both instrument-based and visual-based shade-matching systems can be more fully appreciated by considering the difficulties involved in matching the appearance of human teeth. Tooth color itself results from a relatively complex interaction of reflection, transmission, refraction, fluorescence, and scattering by a variety of organic and inorganic components. It is influenced by variations in tooth pulp volume, dentin condition, enamel composition, and other variations in the composition, structure, and thickness of the dental tissues. One result of this complexity is that color appearance and color measurement are greatly influenced by lighting geometry, spectrum, surrounding colors, and other environmental factors.

As a further complication, color within a single tooth is generally not uniform. Color non-uniformities can result from spatial variations in composition, structure, thickness, internal and external stains, surface texture, fissures, cracks, and degree of wetness. As a result, measurements taken over relatively large areas produce averaged values that may not be representative of a tooth's dominant color. In addition, natural color variations and non-uniformities make it unlikely that a given tooth can be matched exactly by any single shade tab. This means that a method for conveying the distribution of color within a tooth, not just its average color, is required. Further, tooth color is seldom uniform from tooth to tooth. Therefore, the ideal color of a restoration may not be in visual harmony with that of an adjacent tooth or of any other single tooth in a patient's mouth. Moreover, people generally are particular about the appearance of their teeth. Understandably, they are quite intolerant of restorations that appear inappropriate in color.

In cosmetic dentistry, the fabrication lab often requires additional information in order to more accurately map tooth color in addition to simple shade matching. In practice, the dentist or technician may provide a photograph in addition to a shade tab, so that the fabrication lab can adjust color characteristics over different portions of the tooth. This helps to provide a type of color mapping for subjective use, with information that relates to the shade tab and shows how colors in other portions of the tooth vary from that of the shade tab.

It is often difficult to decide which tab matches most closely (or, conversely, which has the least mismatch) and to provide accurate information on color variation over the tooth surface. Frequently, the practitioner determines that the patient's teeth are particularly difficult to match, requiring that the patient go in person to the laboratory that will be fabricating the restoration. There, trained laboratory personnel can perform the color match and color mapping. In many cases, the patient may even need to return to the dentist and laboratory two, three, or even more times as the color of the prosthesis is fine tuned by sequential additions of ceramics or other colored materials. In a high percentage of cases, estimated to be nearly 10% for some dental prostheses, the visual color matching procedure still fails and the prosthesis that has been fabricated is rejected for color or visual harmony by the dentist or by the patient.

Considering the relative difficulty of the color matching task, and the further complexity of color mapping, a high rate of failure is not at all surprising. Visual color evaluation of relatively small color differences is always difficult, and the conditions under which dental color evaluations must be made are likely to give rise to a number of complicating psychophysical effects such as local chromatic adaptation, local brightness adaptation, and lateral-brightness adaptation. Moreover, shade tabs provide at best a metameric (that is, non-spectral) match to real teeth; thus, the matching is illuminant-sensitive and subject to variability due to normal variations in human color vision, such as observer metamerism, for example.

In response to the need for improved color matching and color mapping in dental applications, a number of approaches have been attempted. Some solutions to this problem are of the following general types:

(i) RGB-based devices. With this approach, an image of the entire tooth is captured under white light illumination using a color sensor. Tristimulus values are calculated over areas of the tooth surface from RGB (Red, Green, Blue) values of the 3-color channels of sensor, making use of a color calibration transform. Color analysis by RGB-based devices relies heavily on the quality of the captured image and requires robust calibration and may require use of the same camera for color-matching of tooth and prosthetic device. This requirement can be due to calibration of the camera itself as well as to color preprocessing that is performed within the camera in order to provide the RGB data; this preprocessing can vary significantly from one camera to the next, even for cameras from the same manufacturer. Maintaining accuracy tends to be difficult due to metamerism, in which the color measured is highly dependent upon the illuminant. This is particularly troublesome since dental measurement and imaging are generally carried out under conditions that differ significantly from natural lighting conditions. Examples using RGB measurement and employing a corresponding color transform in this way include: U.S. Pat. No. 5,766,006 entitled "Tooth Shade Analyzer System and Methods" to Murljacic; U.S. Pat. No. 6,008,905 entitled "Method and Apparatus for Determining the Appearance of an Object" to Breton, et al.; and U.S. Pat. No. 7,064,830 entitled "Dental Color Imaging System" to Giorgianni et al.

(ii) Colorimetric devices. Devices of this type are engineered to directly measure color as perceived by the human eye. With this type of device, illuminating light or reflected light (under white light illumination) is filtered at the three wavelength bands that correspond to the spectral response characteristic or color matching functions of the eye, and measured reflected signals are directly translated into tristimulus values. As with RGB-based devices described in (i), measurements from this type of device also suffer from metamerism. Some examples using this approach include those disclosed in U.S. Pat. No. 5,383,020 entitled "Method and Apparatus for Determining the Color of a Translucent Object Such as a Tooth" to Vieillefosse that requires a spectrometer and U.S. Pat. No. 6,867,864 entitled "Optical Measurement Device and Related Process" to Overbeck et al.

(iii) Spectrophotometric devices. These devices employ spectral reflectance for obtaining color data. Illuminating or reflected light is spectrally scanned, and light reflected by the tooth is recorded, using a photosensor, as a function of wavelength. Visual color, that is, CIE (Commission Internationale de L'Éclairage or International Commission on Illumination) tristimulus color information, is then calculated from the measured spectral reflectance curve. Spectrophotometric devices are not subject to the same tendency to metamerism inherent to colorimetric and RGB-based devices and, potentially, yield more accurate color measurements. It is significant to note, however, that the spectrophotometer is not an imaging device. The spectrophotometer is an instrument that measures the spectral content of incoming light over a small area using a photosensor. Examples of tooth color measurement using spectrophotometric devices include U.S. Pat. No. 4,836,674 entitled "Method and Apparatus for Determining Color, in Particular of a Dental Prosthesis" and U.S. Pat. No. 6,038,024 entitled "Method and Apparatus for Determining the Color Stimulus Specification of an Object" to Berner.

Although the data obtained using the spectrophotometric approach provides advantages for more accurate color matching over colorimetric and RGB approaches, including elimination of metamerism, this approach has been found difficult to implement in practice. The use of a light scanning component for measuring different spectral components, generally employing a grating or filter wheel, tends to make the spectrophotometric system fairly bulky and complex. This makes it difficult to measure teeth toward the back of the mouth, for example. Attempts to alleviate this problem have not shown great success. As one example, U.S. Pat. No. 5,745,229 entitled "Apparatus for Determining Optical Characteristics of an Object" to Jung et al. provides a compact spectrophotometric device employing optical fibers to channel reflected light to an array of sensors, each sensor using a different spectral filter. However, as is true of spectrophotometric devices in general (iii, above), this device measures only a small area of the tooth surface at a time. To obtain a color mapping of an entire tooth surface requires numerous separate measurements with this approach. The image capture process is time-consuming and does not provide consistent results. Color mappings can be inaccurate using such an approach, since there can be considerable sensitivity to illumination and image capture angles and probe orientation during the imaging process.

In general, conventional methods that employ color filters, either at the illuminant end or at the sensor end, can be less desirable because they are subject to the limitations of the filter itself.

Thus, there is a need for an improved measurement apparatus that provides dental shade matching and mapping in a procedure that is straightforward to execute, having a high degree of accuracy, but without high cost or complex components.

SUMMARY OF THE INVENTION

An object of the present invention is to advance the art of color shade mapping in dental applications. With this object in mind, the present invention provides an apparatus and method that obtains spectral reflectance data from multi-color images of the tooth without the complexity of using a spectrophotometer.

An advantage of the present invention is that it employs an imaging array for obtaining spectrophotometric measurements over the full image. This makes embodiments of the present invention readily adaptable for intraoral camera use. In addition, the output spectrophotometric color data that is provided is not subject to metamerism, which affects solutions that use colorimetric and RGB color matching techniques. The approach used in embodiments of the present invention obtains spectral reflectance data for each pixel of the tooth image, allowing accurate mapping of tooth color, including variation in color over different portions of the tooth.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for generating a color mapping for a dental object, executed at least in part by a control logic processor, comprising: generating a transformation matrix according to a set of spectral reflectance data for a statistically valid sampling of teeth; directing illumination toward the dental object over at least a first, a second, and a third wavelength band, one wavelength band at a time; obtaining, for each of a plurality of pixels in an imaging array, an image data value corresponding to each of the at least first, second, and third wavelength bands; applying the transformation matrix to form the color mapping by generating a set of visual color values for each of the plurality of pixels according to the obtained image data values and according to image data values obtained from a reference object at the at least first, second, and third wavelength bands; and storing the color mapping in a computer-accessible electronic memory.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
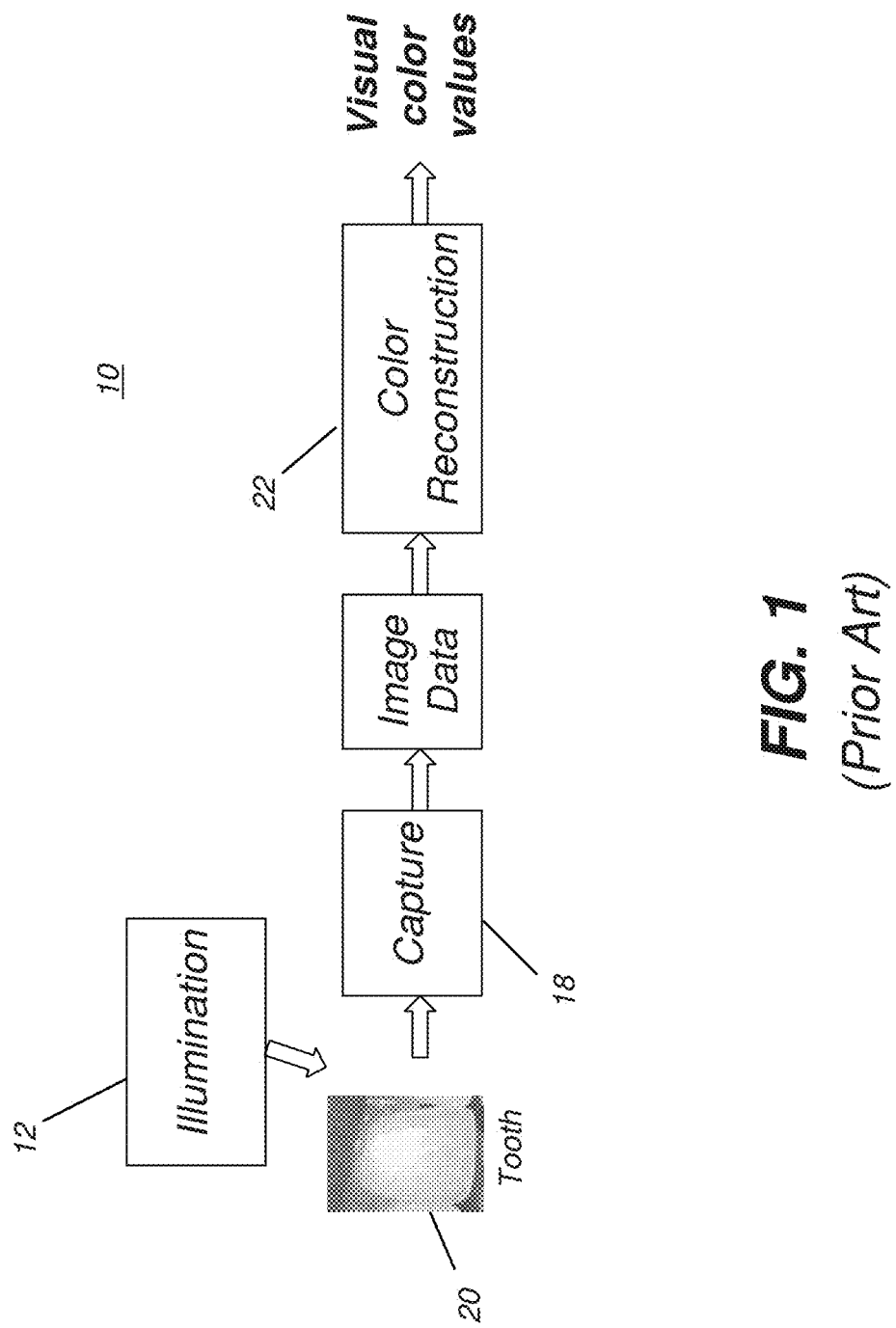
FIG. 1 is a schematic diagram showing the arrangement of components in a conventional image-based apparatus for obtaining a color measurement for a tooth.

The following is a detailed description of the preferred embodiments of the invention, reference being made to the drawings in which the same reference numerals identify the same elements of structure in each of the several figures.

In the context of the present application, the term "narrow band" is used to describe LED or other illumination sources that emit most of their output light over a narrow range of wavelengths, such as 20-50 nm wide. The term "broadband" is used to describe a light sensor that exhibits high sensitivity to incident light over a wide wavelength range extending at least from about 400 nm to about 700 nm. Because this type of sensor responds to light but does not distinguish color, it is often referred to as a "monochrome" sensor or, somewhat inaccurately, as a "black-and-white" sensor.

In the context of the present application, the term "pixel", for "pixel element", has its common meaning as the term is understood to those skilled in the image processing arts. An electronic image of an object is captured by an array of light-sensitive elements, each of which provides the signal for forming a pixel of image data.

Figures shown and described herein are provided in order to illustrate key principles of operation and component relationships along their respective optical paths according to the present invention and are not drawn with intent to show actual size or scale. Some exaggeration may be necessary in order to emphasize basic structural relationships or principles of operation. Some conventional components that would be needed for implementation of the described embodiments, such as various types of optical mounts, for example, are not shown in the drawings in order to simplify description of the invention itself. In the drawings and text that follow, like components are designated with like reference numerals, and similar descriptions concerning components and arrangement or interaction of components already described are omitted. Where they are used, the terms "first", "second", and so on, do not necessarily denote any ordinal or priority relation, but are simply used to more clearly distinguish one element from another.

The terms "color" and "wavelength band" are generally synonymous as used in the context of the present disclosure. For example, a laser or other solid-state light source is referred to by its general color, such as Red, rather than by its peak output wavelength (such as 635 nm) or its wavelength band (such as 630-640 nm).

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members. For a set S, a subset may comprise the complete set S. A "proper subset" of set S, however, is strictly contained in set S and excludes at least one member of set S.

In the context of the present disclosure, the term "dental object" refers to an object, material, or other element for intra-oral use or application and includes teeth, prosthetic devices such as crowns, dentures, braces and other supports and bridges, filling materials, shade-matching tabs, and the like.

In contrast to some attempts at characterizing tooth color, the apparatus and methods of the present invention take into account a combination of factors that affect color measurement and that complicate the task of accurately characterizing color. Particular embodiments of the present invention identify and compensate for variable factors such as illumination wavelengths and detector response characteristics in order to derive accurate color data. To do this, the approach that is used in embodiments of the present invention obtains, for each pixel in the image of a tooth or other dental object, spectral reflectance data that is substantially independent of the spectral response of the measurement device and that can be used to provide an objective measure of color that applies for illuminant over any combination of wavelengths. As a result, the data that is obtained for tooth color mapping in the present invention can be used to reconstruct the visual color of an object when viewed under any illuminant taken from a set of available illuminants with known spectral distributions. The color mapping that is generated for a dental object can then be used for generating a displayed image or used for comparison against color mapping data for another object or material, such as a crown or other dental prosthetic device or a filling material. The color mapping that is generated for a dental object can also be used for designing and forming a dental prosthetic device, for example. A color mapping for a tooth or other dental object can consist of a considerable amount of data and is typically stored as a data file in a computer-accessible memory.

Referring to FIG. 1, there is shown a schematic block diagram of a conventional imaging apparatus 10 for obtaining dental color data. An illumination source 12 directs light onto a tooth 20. A capture module 18 then performs image capture and provides image data to a color reconstruction module 22. The output is a set of visual color values that correspond to points on the tooth surface.

Figure 2:
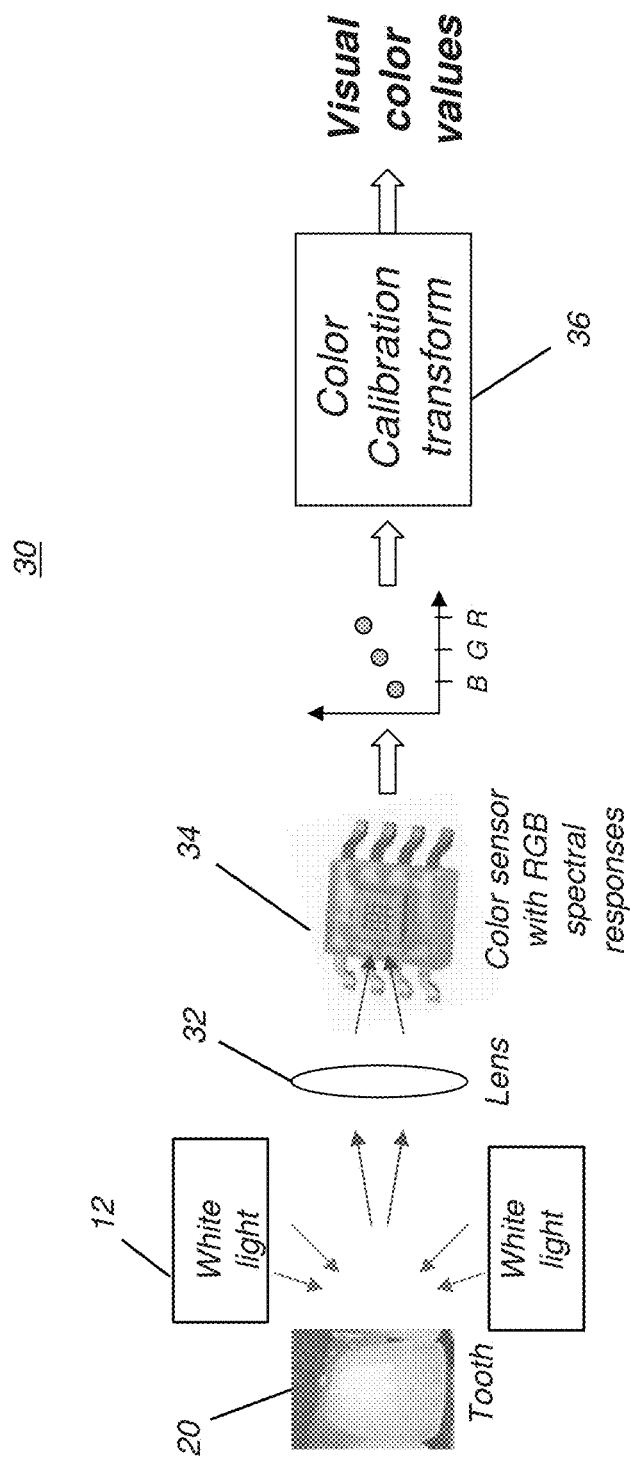
FIG. 2 is a schematic diagram showing an earlier method that makes use of a color calibration transform for obtaining tooth color values.

The basic arrangement of FIG. 1 is used for each of the image-based color measurement approaches described earlier in the background section. FIG. 2, for example, shows a schematic diagram for implementing the system described in the Giorgianni et al. '830 patent cited earlier. In an imaging apparatus 30, illumination source 12 provides white light illumination to tooth 20. A lens 32 directs reflected light to a sensor 34 that provides corresponding Red, Green, and Blue values for each pixel. A color calibration transform 36 then generates visual color values as output for every image point.

In contrast to the approaches shown in FIGS. 1 and 2, the apparatus and methods of the present invention provide a color mapping apparatus that utilizes color reconstruction based on spectral reflectance. This approach is advantaged over RGB-based and colorimetric devices by providing an inherently more accurate set of data on the actual color characteristics of the tooth. Advantageously, this method is not subject to metamerism, which would otherwise render measurements dependent on the illuminant of the measuring system. Unlike spectrophotometric measurement devices in general, the apparatus and method of the present invention obtain spectral data for each pixel in the tooth image. Moreover, this information is obtained using an imaging array rather than a photosensor. The imaging array used in embodiments of the present invention is a monochrome sensor, although a color sensor can alternatively be used.

The apparatus and methods of the present invention obtain not only an accurate color measurement for a single pixel or grouping of adjacent pixels, but, because they use an imaging device, also provide suitable information for accurate color mapping over the full image of the dental object. By obtaining spectral measurement data using an imaging array, embodiments of the present invention obtain measurements that allow spectral data to be generated for each pixel of the tooth image.

Figure 3:
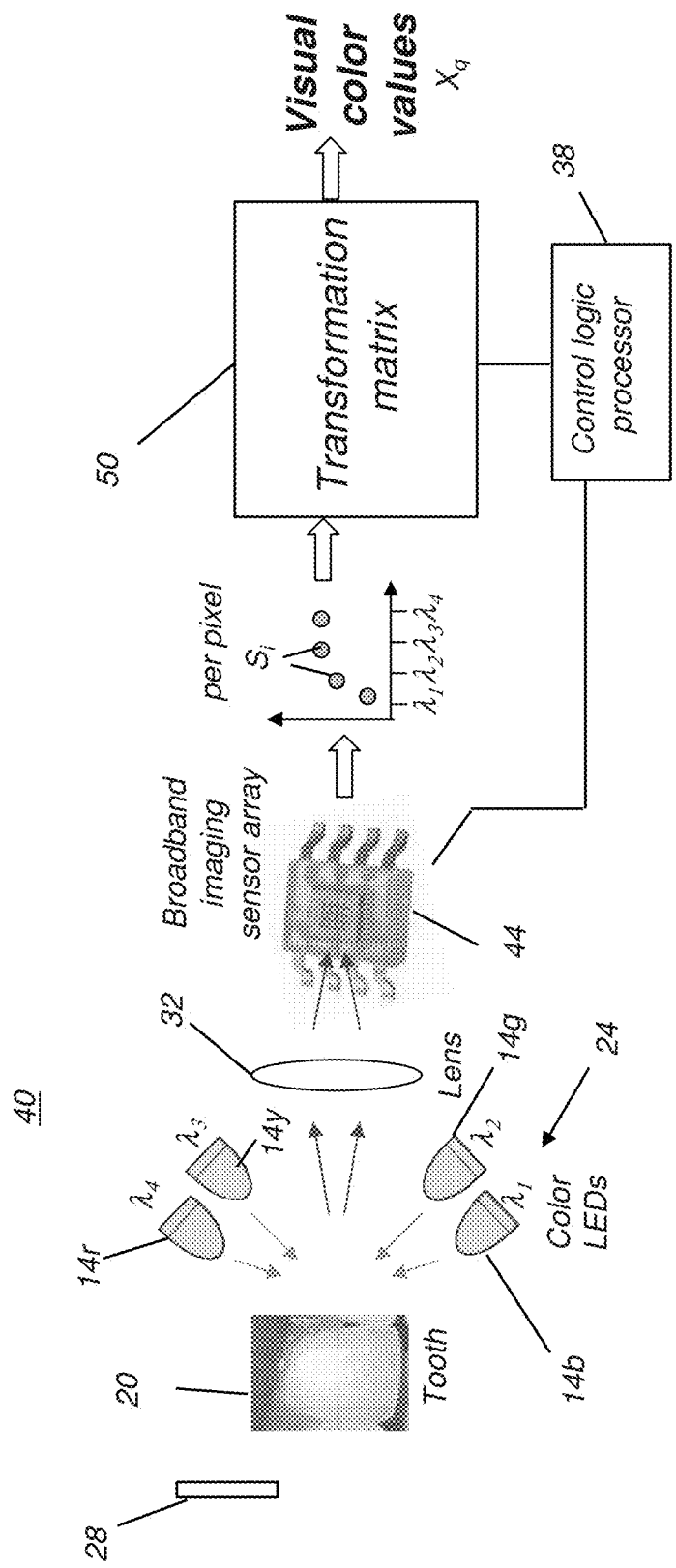
FIG. 3 is a schematic block diagram that shows a color mapping apparatus according to one embodiment of the present invention.

Referring to the schematic diagram of FIG. 3, a color measuring and mapping apparatus 40 uses an illumination apparatus 24 that can provide light of separate colors. In one embodiment, illumination apparatus 24 consists of multiple narrow band light sources 14$b$, 14$g$, 14$y$, and 14$r$, shown as color LEDs, having wavelength bands $\lambda 1$, $\lambda 2$, $\lambda 3$, and $\lambda 4$, respectively. In the embodiment of FIG. 3, four LEDs are shown by way of example; there can be any number of different colors and more than a single LED or other light source for each color. A broadband imaging sensor array 44, a CCD (charge-coupled device) or CMOS (Complementary Metal-Oxide Semiconductor) imaging array in this embodiment, provides a set of output values for each pixel corresponding to reflection from each narrow band light source. A reference target 28 is an object that is optionally provided for obtaining reference intensity measurements used in correcting for intensity fluctuations in the system, as described subsequently. In one embodiment, reference target 28 is a gray patch, with known spectral reflectance characteristics. Reference target 28 and tooth 20 are both within the field of view of imaging lens 32. In an alternate embodiment, reference target 28 is an object that does not appear in the image field, but is a separate device used for obtaining reference and calibration data.

In order to obtain the spectral data using the apparatus shown in FIG. 3, the LEDs or other light sources can be energized according to color groups, one color group at a time in rapid succession, and the corresponding measurements of reflected light are obtained by imaging sensor array 44. As shown in thumbnail form in FIG. 3, this effectively provides, for each pixel of the tooth image, a number of points on a graph, one intensity reading corresponding to each of wavelength bands $\lambda 1$, $\lambda 2$, $\lambda 3$, and $\lambda 4$ in this example. A statistics-based transformation matrix 50 is used to generate the full spectral reflectance curve using these points. The result is a spectral reflectance curve for each individual pixel of the tooth image. These data provide a color mapping that more accurately represents a color shade as compared to other methods that simply attempt to measure tristimulus values directly or perform color conversion from RGB to a standard color space, such as hue-saturation-brightness value (HSV) or Commission Internationale de L'Éclairage L*a*b* (CIELAB) color space, for example. Also shown in FIG. 3 is control logic processor 38, which performs control logic processing and contains supporting computer-accessible electronic memory components that execute these processing functions and store interim and final results. Such components are familiar to those skilled in the imaging arts.

Figure 4A:
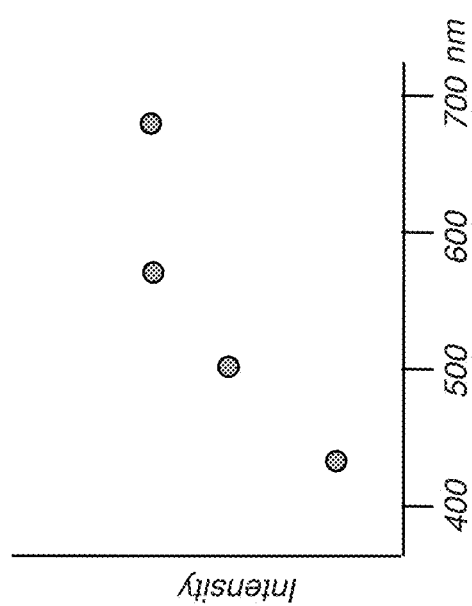
FIG. 4A is a graph showing intensity measurements related to specific wavelengths.

The graph of FIG. 4A shows an example in which four discrete intensity measurements are obtained for a pixel, one for each light source 14$b$, 14$g$, 14$y$, and 14$r$, corresponding respectively to wavelength bands $\lambda 1$, $\lambda 2$, $\lambda 3$, $\lambda 4$. This yields four points in a graph of intensity vs. wavelength, as shown.

Figure 4B:
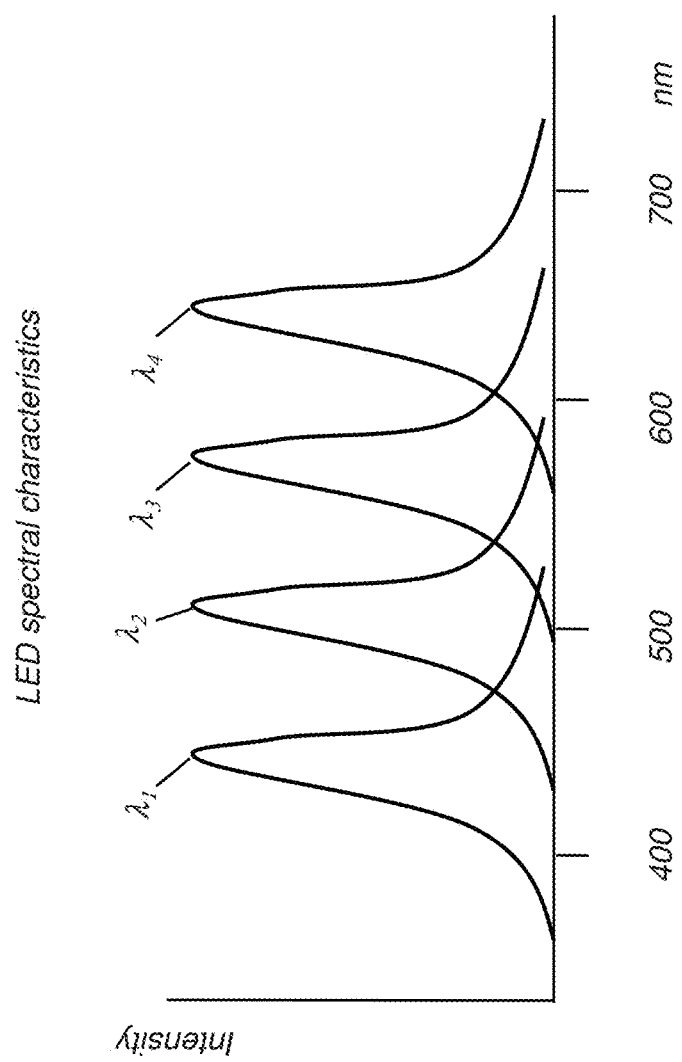
FIG. 4B is a graph showing typical spectral characteristics for light sources used in one embodiment.

Taking accurate measurements requires knowledge of different energy levels and measurement sensitivities in the system. As FIG. 4B shows, each narrow-band light source, an LED in this embodiment, provides an output intensity over a constrained range. Wavelength bands $\lambda 1$, $\lambda 2$, $\lambda 3$, and $\lambda 4$ are identified by the nominal wavelengths at which these intensity curves peak.

Figure 4C:
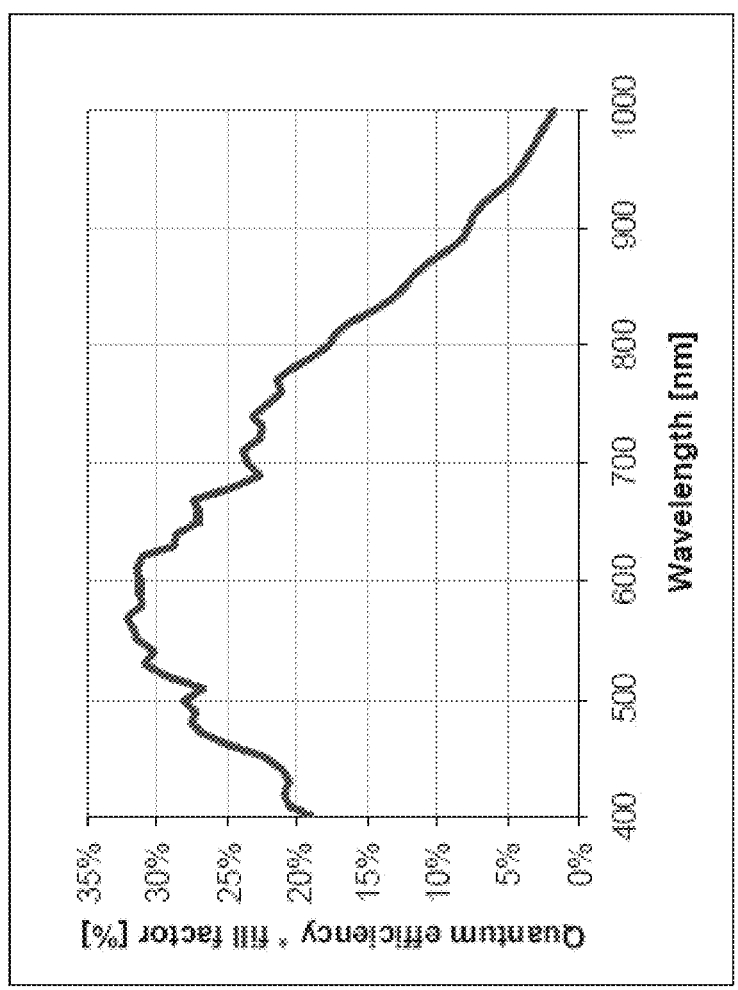
FIG. 4C is a graph showing a spectral response characteristic for a broadband sensor array in one embodiment.

Broadband sensor array 44 can be any type of sensor array that measures the amount of reflected light that corresponds to the illumination apparatus 24 component that is energized and that provides a measured value for each pixel. In one embodiment, broadband sensor array 44 has a broad spectral response characteristic over the visible wavelength range. This is distinctly different from the "color matching functions" of the eye or the spectral response of a color sensor array, both of which have significant values only in isolated bands of the visible wavelengths. For example, the monochrome CCD imaging array may have a typical quantum efficiency curve as shown in the example of FIG. 4C. This device measures the amount of reflected light that corresponds to each light source 14$b$, 14$g$, 14$y$, and 14$r$, as it is illuminated and provides an output signal that is indicative of the sensed light intensity received. Because the peak wavelength and bandwidth of the LED light source is known, the measured value can be readily associated with a wavelength, without the need for a color filter array (CFA) or other filtering component.

Figure 5A:
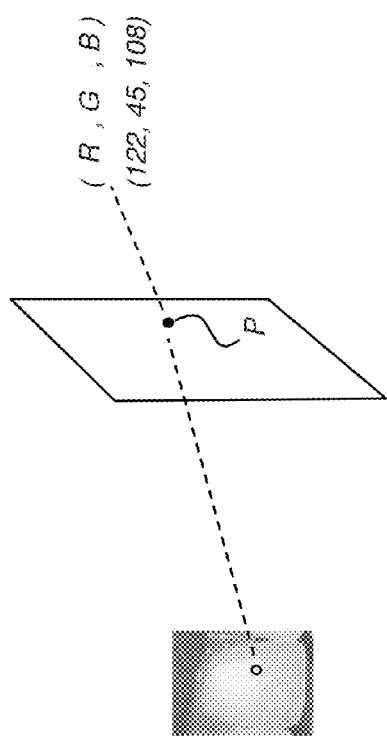
FIG. 5A is a schematic diagram showing the tristimulus data obtained for each pixel using conventional color matching.
Figure 5B:
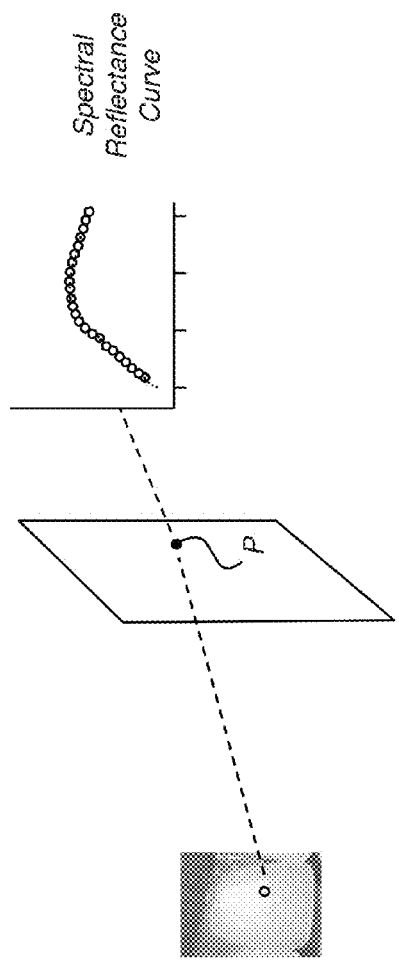
FIG. 5B is a schematic diagram showing the spectral reflectance data obtained for each pixel using the apparatus and methods of the present invention.

In contrast to some color-matching solutions, the method and apparatus of the present invention provide a spectrophotometric or spectral reflectance color mapping that effectively stores, for each pixel in the tooth image, estimated spectral reflectance data values $R_{(tooth)}$ that can be used to accurately profile the color of the tooth surface. By comparison against conventional methods that rely on RGB calibration transform or colorimetric measurements, the methods of the present invention are capable of generating a mapping that includes a considerable amount of data for each pixel of the tooth image. This is represented schematically in FIGS. 5A and 5B. FIG. 5A shows the color data gathered for a single pixel P using conventional color-measuring approaches. In the example shown, a single data value is provided for each of the Red, Green, and Blue color planes. By contrast, FIG. 5B shows the nature of the spectral reflectance mapping data that is obtained for each pixel using the methods of the present invention. Here, each pixel P effectively has an associated spectral reflectance curve that provides a substantial amount of information on its actual color content, from which tristimulus values X, Y, Z or other color data can be derived. In practice, only a small amount of data may actually be stored in memory for each pixel P following this processing; the spectral reflectance curve itself can be reconstructed using the stored matrix of coefficients obtained as described earlier. In memory storage, then, each pixel can be associated with a set of spectral reflectance values and, optionally, also have a link or other identifier for a matrix that is capable of re-creating the full spectral reflectance curve for that pixel. Alternately, calculated tristimulus values, CIELAB values, or values in other standard color space could be stored for each pixel P.

One advantageous result of having spectral reflectance data values is improved color matching between dental objects, such as between a tooth and a prosthetic device or material. Using the data acquisition and processing sequence of the present invention, color matching can be accomplished using any of a number of mathematical techniques. In one embodiment, the spectral reflectance curve for a dental object A is compared with the spectral reflectance curve for a dental object B and differences between the two curves are evaluated for closeness of fit or other metric. For example, the overlap area between two curves over different wavelength ranges can be evaluated. In other embodiments, tristimulus data values or CIELAB color values are obtained for each of the dental objects and are compared.

General theory and principles of obtaining spectral reflectance data for pixels in an image, using multiple narrow-band measurements from a multispectral camera, were demonstrated and described by Peter D. Burns and Roy S. Berns in an article entitled "Analysis Multispectral Image Capture", *Fourth Color Imaging Conference: Color Science Systems and Applications*, 1996, pp. 19-22. These researchers utilized a white light source with seven interference spectral filters, successively switched into position, to obtain image data from a set of color reference samples at different wavelengths. Principal Component Analysis (PCA) was then applied to provide a set of scalar values usable for reconstructing spectral reflectance data for an unknown color patch, using a similarly obtained sequence of color images. Although the work of these researchers showed the feasibility of using a small number of measurements for obtaining accurate spectral reflectance data, the system employed would be impractical for color mapping of teeth and other dental objects and materials. The design of a multispectral camera utilizing multiple switched interference filters is not compatible with the size and access constraints of dental imaging.

Figure 6A:
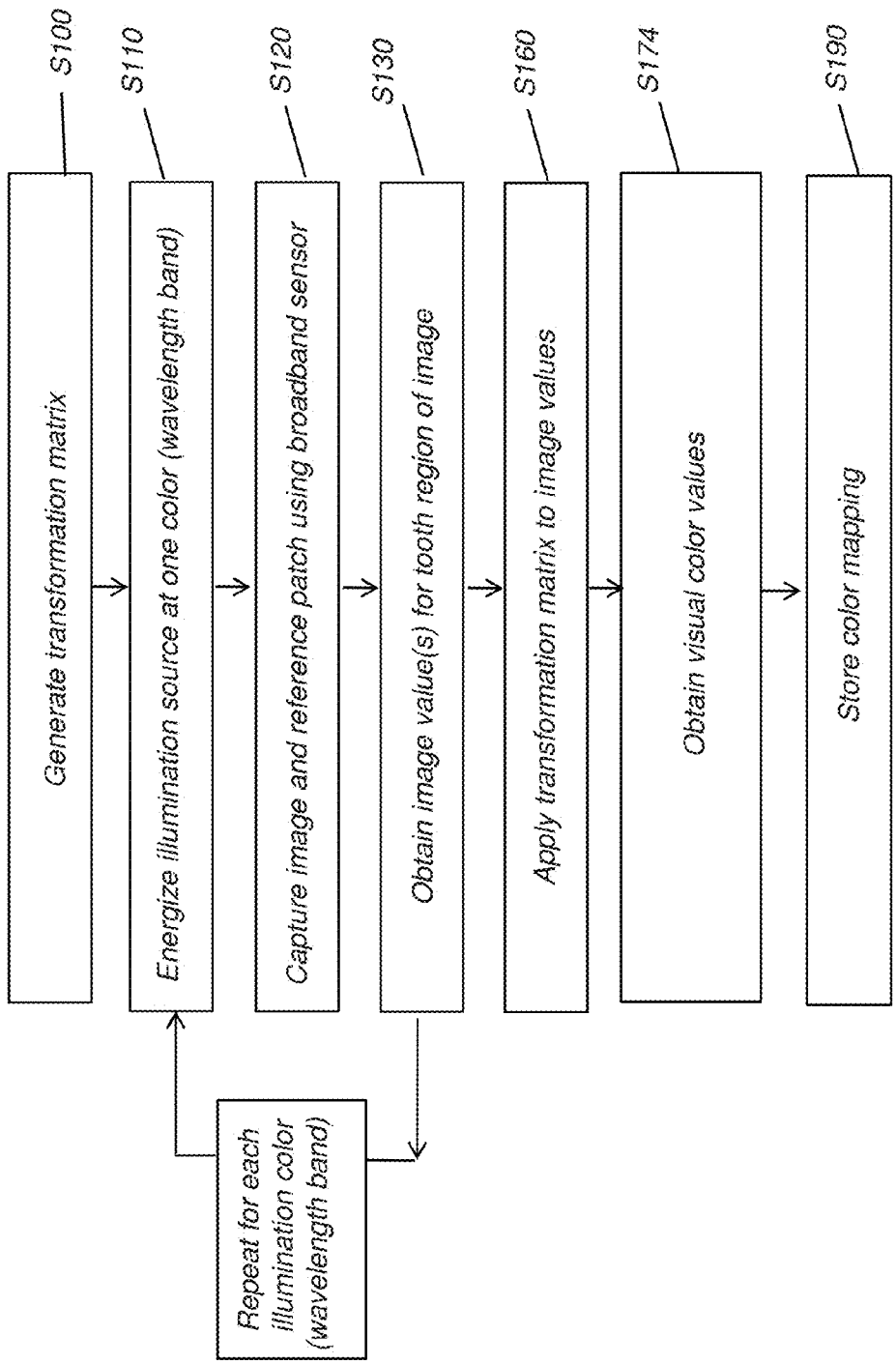
FIG. 6A is a logic flow diagram of steps for obtaining visual color mapping data from a tooth.

The logic flow diagram of FIG. 6A shows steps executed by control logic processing components in color measuring and mapping apparatus 40 of FIG. 3 for generating visual color values for a tooth in one embodiment of the present invention. A transformation matrix generation step S100 initially executes using spectral reflectance data from the statistically valid sampling of teeth, as described subsequently. A looping procedure executes once per source color, here for each LED color or other narrow-band illumination source. In an illumination step S110, the LED or other narrow-band illumination source is energized. An image capture step S120 obtains an image of tooth 20 and, optionally, of reference target 28 at the given illumination. The resulting image consists of light reflected from the tooth, captured for each pixel in image capture step S120. The array of image values measured from the broadband sensor array is then obtained and stored in an obtain values step S130. The loop consisting of steps S110, S120, and S130 repeats until each color group of LEDs or other narrow-band light source has been energized. The net result is a set of image values for each pixel of the image for the tooth or other dental object.

Obtain values step S130 results in the set of N signals for N image wavelength values $s=\{s_1, s_2, \ldots, s_k\}$. Alternatively, step S130 can include additional signal values based on transformations of the above signal values, for example polynomial transformations, $s=\{s_1, s_2, \ldots, s_k, s_1^e, s_k^e, \ldots s_k^e\}$, where e is a real number. Alternately, the transformed values of the image sample measurements can be calculated using a simple power law with the exponent in the range [0.3-0.4].

Continuing with the logic flow in FIG. 6A, a matrix application step S160 applies a transformation matrix to the measured image values. An obtain visual color values step S174 generates visual color values from the image data according to the transformation matrix. The color mapping that is generated is then stored in an electronic memory by control logic processor 38 in a storage step S190. The memory itself can be a random-access device, for short-term storage, or an optical or magnetic storage unit, for longer-term storage. The color mapping can be generated as needed, so that memory storage as shown in FIG. 6A is a temporary "workspace", and is used by control logic processor 38 only for the duration of performing a color match or comparison, or during display of an image for example. Alternately, storage step S190 can store a color mapping for a longer term, such as part of a database of color mappings, indexed by illuminant types, for example. Once the color mapping is formed and is available in computer-accessible memory, it can be used for comparison against color mapping data for a prosthetic device or material, for example.

Figure 6B:
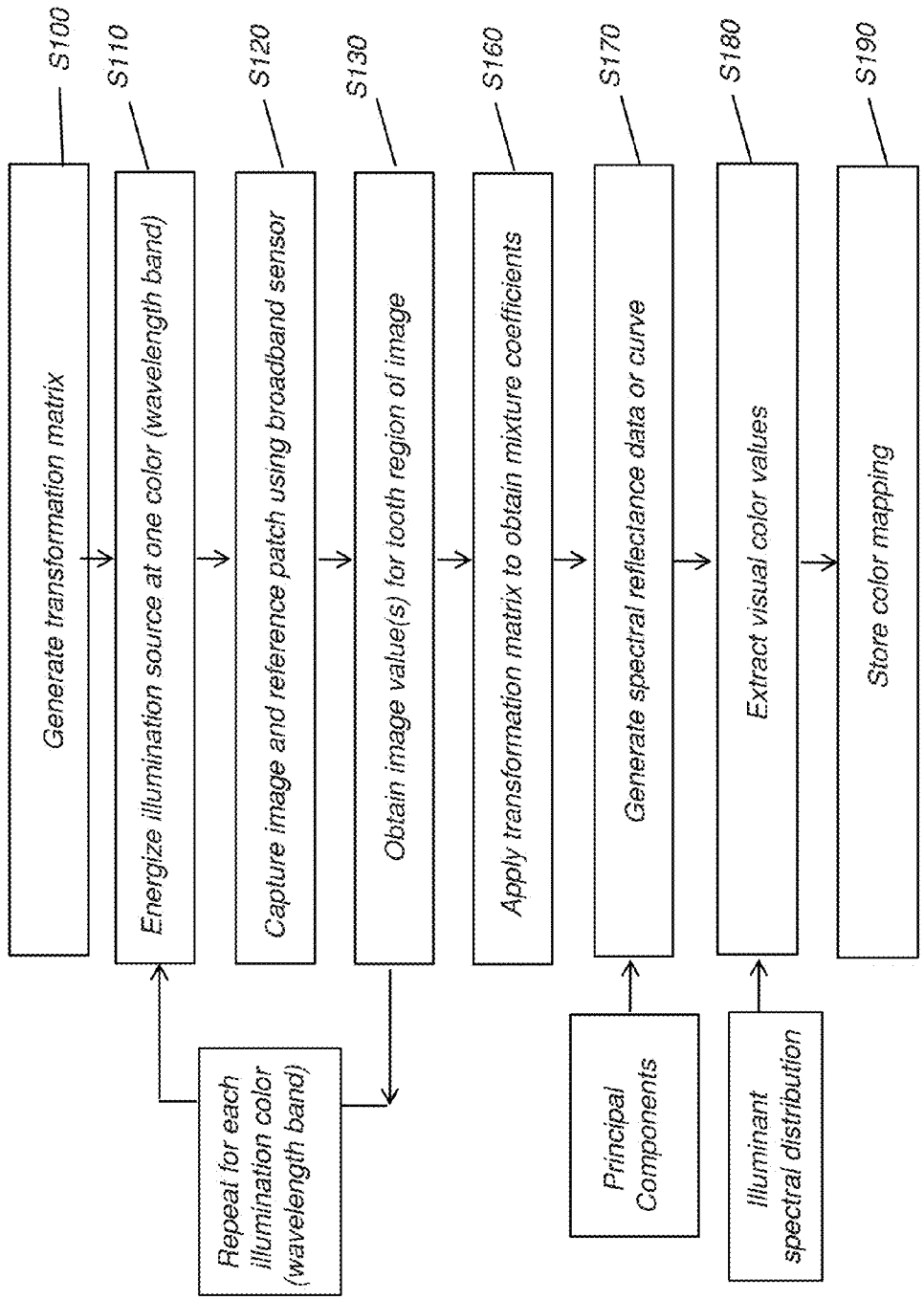
FIG. 6B is a logic flow diagram of steps for obtaining spectral reflectance data from a tooth in an alternate embodiment.

The logic flow diagram of FIG. 6B shows expanded steps for generating a color mapping in one embodiment. Steps S100-S160 are similar to those described with reference to FIG. 6A. Following application of the transformation matrix in step 160, a step S170 generates spectral reflectance data or curve using the mixture coefficients obtained in step S160 and previously computed principal components. A color value extraction step S180 then extracts visual color values for the color mapping based on the spectral distribution of a desired illuminant.

Advantageously, spectral reflectance for tooth and other dental materials is well-behaved and follows a characteristic pattern. Spectral reflectance curves for teeth and dental materials exhibit a smooth, consistent shape, with variation only within a relatively limited range. This characteristic enables the use of statistical techniques for providing the tools needed for more accurate color matching than is available using conventional approaches.

Generating Transformation Matrix 50

As FIG. 3 showed, transformation matrix 50 is used for providing visual color data based on a relatively small number of measured values for a tooth. Embodiments of the present invention generate transformation matrix 50 from a statistically valid sampling of spectral reflectance data for a large number of teeth. The number of teeth in a "statistically valid sampling" has enough members to be representative of the larger tooth population. Increasing the sample size beyond a statistically sufficient or statistically valid number of samples tends to have no noticeable effect on the resulting data that is obtained from the sampling distribution.

Figure 7:
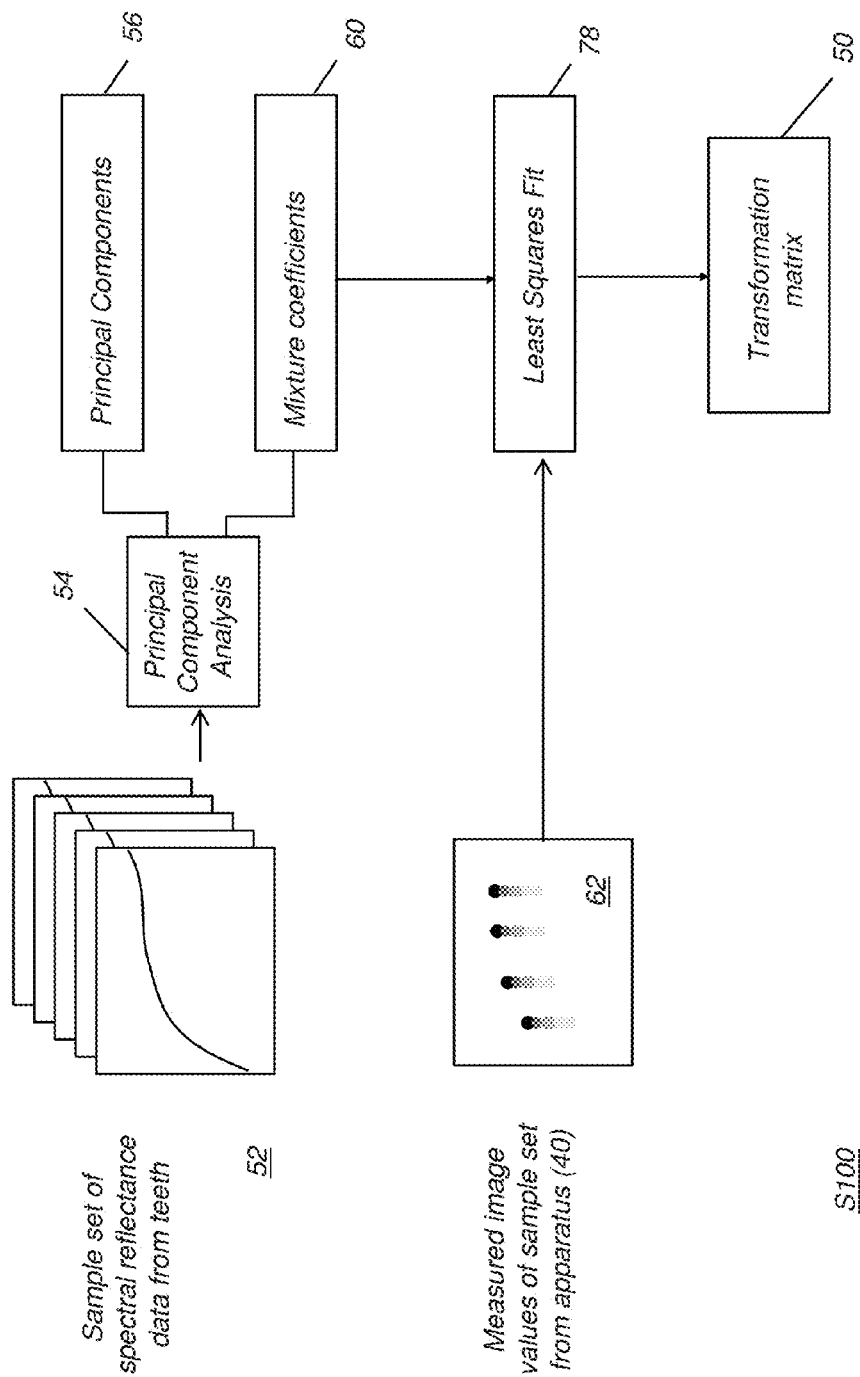
FIG. 7 is a logic flow diagram showing a process for forming a transformation matrix according to one embodiment of the present invention.

Referring to FIG. 7, a process for forming transformation matrix 50 in generate transformation matrix step S100 is shown. Initially, a sample set of spectral reflectance curves 52 is obtained using a spectrophotometer. The sample set contains spectral reflectance curves 52 for a sufficient number of teeth M for use as a statistically valid sample; in one embodiment, M=100, for example. Principal Component Analysis (PCA) shown at 54 is then used to analyze this data to identify those principal components 56 with greatest statistical importance, and the corresponding mixture coefficients 60. Empirical data has shown that the number of significant principal components for spectral reflectance of teeth and other dental objects is about 4.

Principal Component Analysis (PCA) is a well-known vector space transform technique that is used in statistics to reduce the overall number of dimensions for multidimensional data sets in order to better show the relationships in the multidimensional data sets. For multivariate data, such as spectral reflectance data, PCA analyzes the covariance of data variables in order to help uncover trends in the data that can be used in order to better understand the data and to simplify their use. PCA involves a decomposition of data by generating eigenvectors (mutually orthogonal in an $l_2$ norm) that provide an alternate basis or coordinate system for the data. PCA determines an ordered set of eigenvectors, with the ordering based upon decreasing the eigenvalue associated with the respective eigenvector. Since the eigenvectors can be scaled to unit vectors and are orthogonal, an orthogonal linear transformation from its original coordinate system to an alternate coordinate system of eigenvectors is obtained. With this type of data decomposition, the low-order components (that is, the first, second, third, and subsequent principal components in order) represent the most important aspects of the data; higher order components represent increasingly less information about the variance of the data. This enables statistical characterization of the data in a simpler form (that is, at fewer dimensions) than as the data had been originally acquired.

Referring back to FIG. 7, a set of low-order principal components is generated at 56, along with the corresponding set of mixture coefficients 60. Mixture coefficients are used to scale or weight the principal component eignevectors for generating each of the set of teeth spectral reflectance curves for sample set of reflectance curves 52. Simply stated, the mixture coefficients form a vector in the vector space determined by the PCA eigenvectors.

Still referring to the logic flow of FIG. 7, in one embodiment, transformation matrix 50 is generated by taking image value measurements 62 of the M teeth in the sample set using color measuring and mapping apparatus 40 (FIG. 3), at the same locations where the spectral reflectance curves were recorded previously. Four measurements for each of the M teeth are represented at measurements 62 in FIG. 7; the number of measurements that are obtained for each tooth corresponds to the number of light sources (LEDs) in illumination apparatus 24. A least-squares fit procedure 78 is then performed between the set of mixture coefficients 60 and the measured image data, measurements 62, to generate transformation matrix 50, which provides the best-fit matrix for converting measured image data 62 to mixture coefficients 60.

The transformation matrix 50 generation step, according to the embodiment described in FIG. 7, generates a transformation matrix for future use in color mapping. This matrix and the set of principal components 56 are then stored in control logic processor 38 of color measuring and mapping apparatus 40. Then, each time that color measuring and mapping apparatus 40 is used on an unknown tooth, the stored transformation matrix 50 is applied to the obtained image values at pixels of the tooth image to calculate a set of mixture coefficients (step S160), which can then be used with the stored principal components 56 to generate spectral reflectance data (step S170 in FIG. 6B). The generated spectral reflectance curve can then be used with any viewing illuminant's spectral profile and the visual color matching functions to calculate the tristimulus values XYZ of the tooth (step S180 in FIG. 6B).

Figure 8:
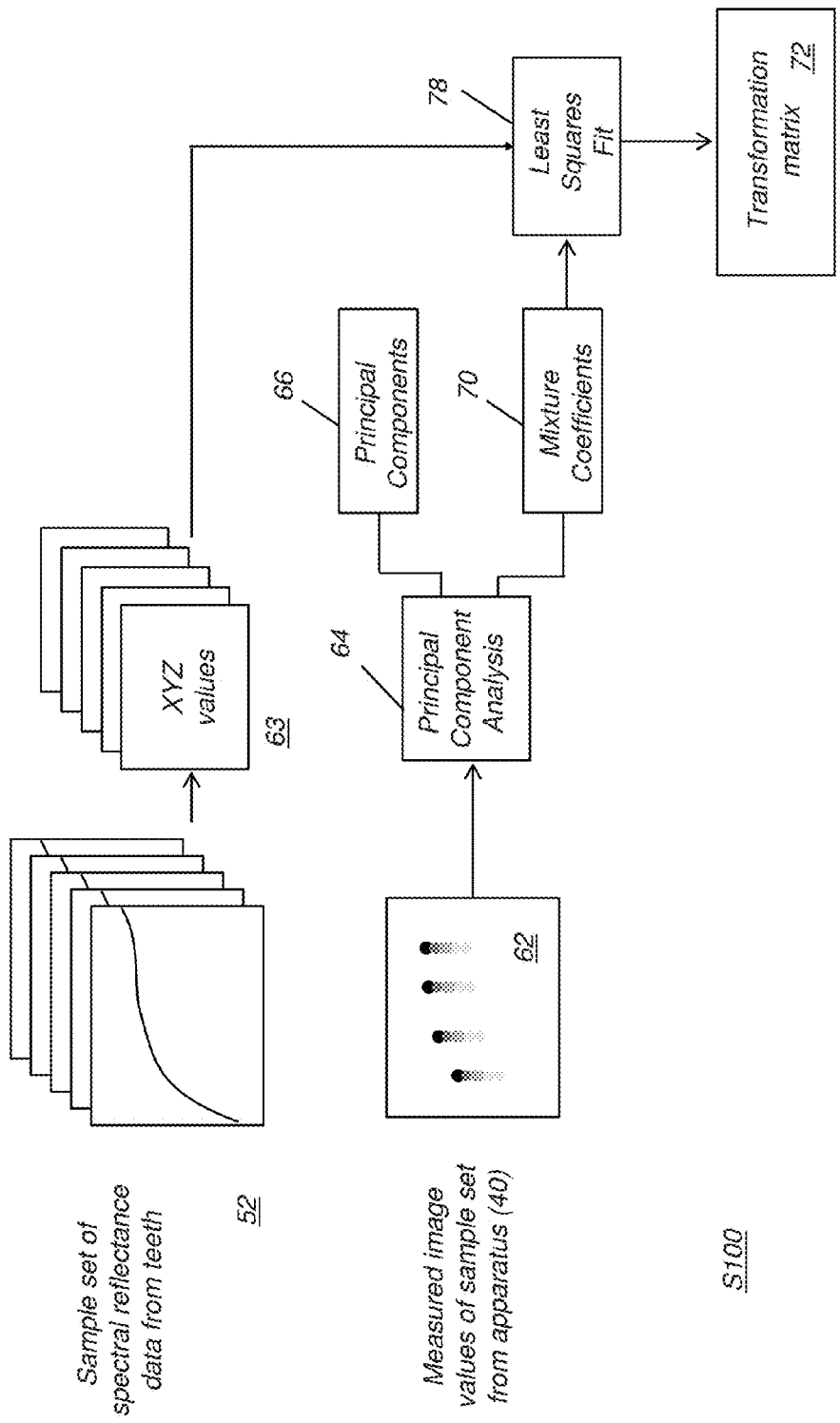
FIG. 8 is a logic flow diagram showing a process for forming a transformation matrix according to an alternate embodiment of the present invention.

In an alternate embodiment for generating a transformation matrix in step S100, as shown in the logic flow diagram of FIG. 8, PCA 64 is performed on the measured image data 62 for the statistically valid sampled set, instead of on the spectral reflectance data 52 from the sample set. Values in measured image data 62 are obtained using mapping apparatus 40 (FIG. 3). The result is the set of significant principal components 66 and the corresponding mixture coefficients 70 for the measured image value data 62. XYZ color values 63 are obtained directly from each curve of the sample set of spectral reflectance data, measured using a spectrophotometer as described earlier. A least squares fit procedure 78 is performed between the obtained XYZ values 63 and the mixture coefficients 70 to generate values for a transformation matrix 72. In this embodiment, transformation matrix 72 is the best-fit matrix for converting mixture coefficients 70, corresponding to the principal components of the measured image data 62, to tristimulus values. This embodiment directly calculates the visual color for a predetermined viewing illuminant; it does not provide complete spectral reflectance information.

Figure 9:
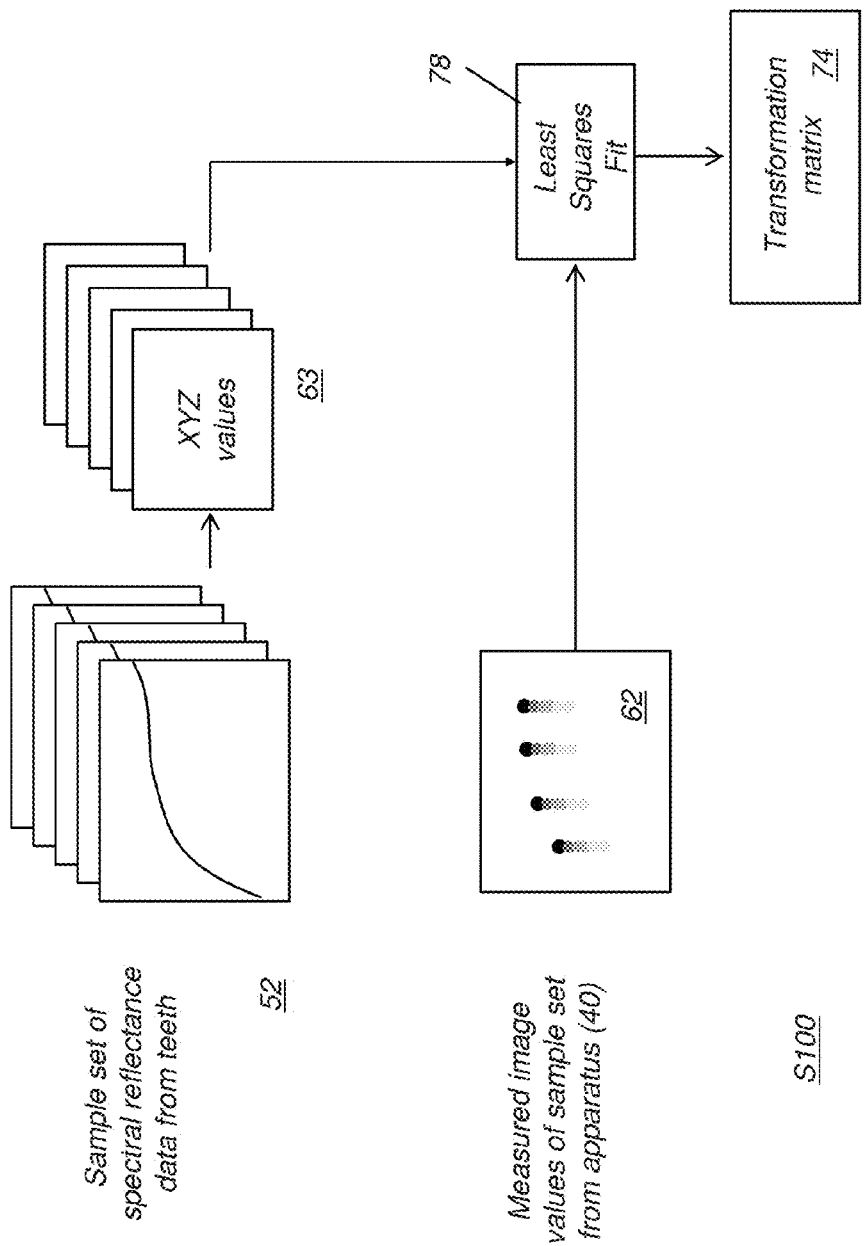
FIG. 9 is a logic flow diagram showing a process for forming a transformation matrix according to another alternate embodiment of the present invention.

FIG. 9 describes another alternate embodiment of step S100 for generating a transformation matrix without performing PCA. XYZ color values 63 are first obtained from each curve of the sample set of spectral reflectance data, recorded using a spectrophotometer as described earlier. Values in measured image data 62 are obtained using mapping apparatus 40 (FIG. 3). A least squares fit is then performed between the obtained XYZ values 63 and the measured image values 62 to generate values for a transformation matrix 74. Transformation matrix 74 in this embodiment is the best-fit matrix for converting the measured image values 62 directly to tristimulus values. It is simpler in implementation than the previous two embodiments described with respect to FIGS. 7 and 8. But unlike the embodiment in FIG. 7, and similar to the embodiment in FIG. 8, this sequence yields only XYZ color values for a predetermined viewing condition.

Figure 10:
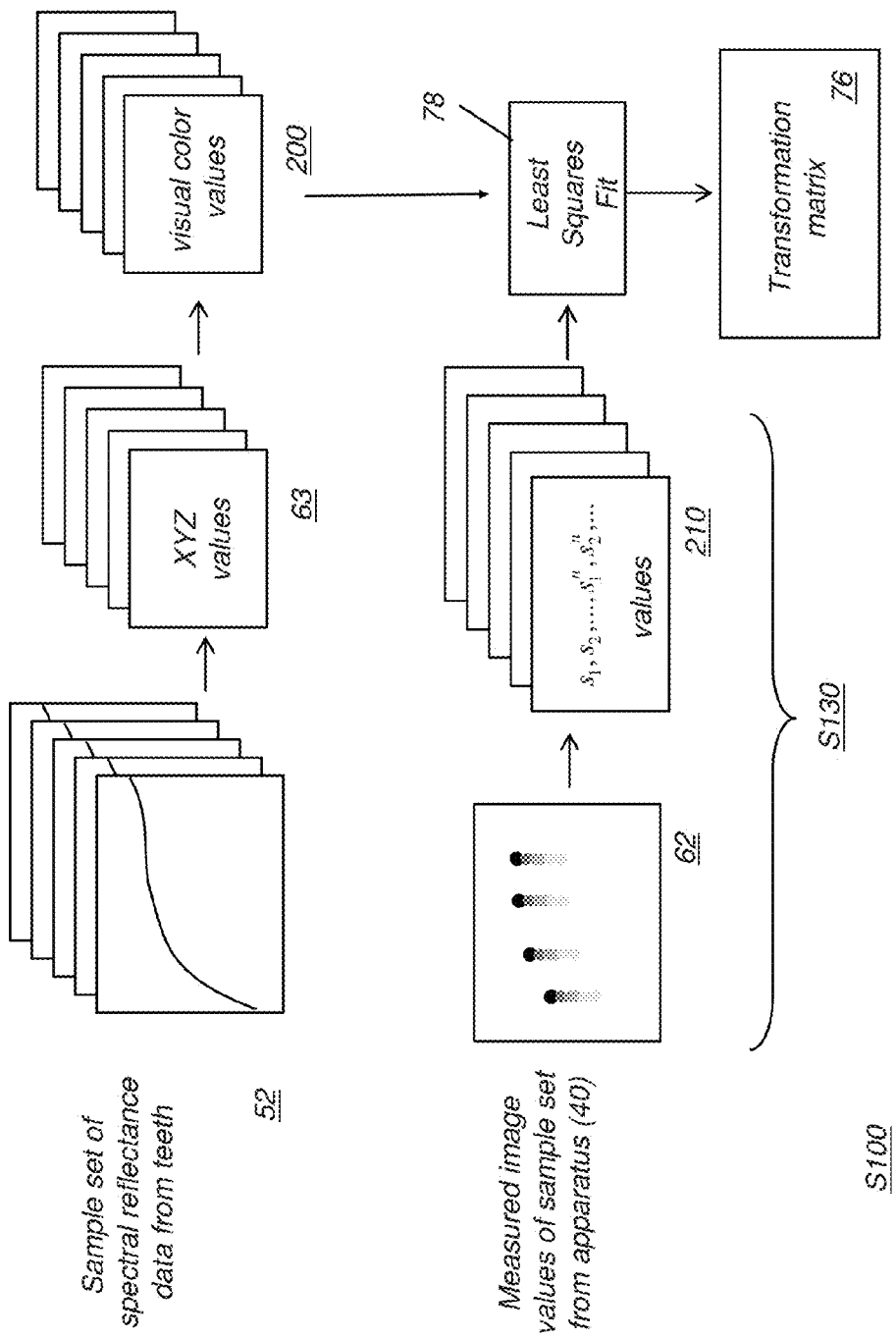
FIG. 10 is a logic flow diagram showing a process for forming a transformation matrix according to yet another alternate embodiment of the present invention.

FIG. 10 describes yet another alternate embodiment of step S100 for generating a transformation matrix without performing PCA. XYZ values 63 are first obtained from each curve of the sample set of spectral reflectance data, recorded using a spectrophotometer, as described earlier. Visual color values 200 are computed for each set of XYZ values. These visual color values can be chosen so that they represent coordinates in an approximately uniform visual color space, such as CIELAB. Values in measured image data 62 are obtained using mapping apparatus 40 (FIG. 3). In this embodiment of step S130, however, the set of measured image data is expanded to include polynomial-transformed values of each measured image value, $s = \{s_1, s_2, \ldots, s_k, s_1^e, s_k^e, \ldots s_k^e\}$, wherein e is a real number, as described earlier. A least squares fit is then performed between the obtained XYZ values 63 and the expanded set of measured image values 210 to generate values for a transformation matrix 76. Transformation matrix 76 in this embodiment is the best-fit matrix for converting the expanded measured image values 210 directly to visual color values. Unlike the embodiments in FIGS. 7, 8 and 9, this sequence yields only visual color values for a predetermined viewing condition.

As has been noted earlier, the task of obtaining accurate color measurement using conventional methods is confounded by variation of illumination and sensor response. These problems are addressed by the improved method of the present invention. The generalized measured signal $S_{i(tooth)}$ that is obtained for a particular wavelength $\lambda$, for LED illumination in the equations that follow, using color measuring and mapping apparatus 40, can be represented as follows:

$$S_{i(tooth)} = \int I_{LEDi}(\lambda)R_0(\lambda)D(\lambda)d\lambda \quad (1)$$

wherein $R_0$ is the actual reflectance of the tooth or other dental object. This variable is also expressed, with reference to the tooth material, as $R_{tooth}$; $D(\lambda)$ is the sensor response; $I_{LEDi}$ is the intensity of the $i^{th}$ LED or other narrow-band light source.

It can be observed that equation (1) holds true for color measurement of the tooth in general, whether using RGB or white light sources and whether the image sensor array is a CCD, CMOS, or other type of light sensing device. It is particularly instructive to note that conventional tooth color measurement devices, such as RGB-based color measurement devices and colorimetric measurement devices, generate the tooth color values from measured signal $S_{i(tooth)}$. As equation (1) shows, however, this signal is itself the product of three variable factors: the actual tooth reflectance $R_0$, the illuminant, and sensor response. It is due to the dependency of this measurement on the light source and on sensor response that accurate color computation is not obtained with a conventional RGB-based or colorimetric measurement apparatus. However, unlike conventional solutions, the approach of the present invention isolates tooth reflectance $R_0$ from the other two factors in the measured signal. The obtained reflectance $R_0$ can then be used to accurately characterize color under any lighting conditions. In this way, the method of the present invention employs a spectrophotometric approach to color characterization. However, unlike conventional spectrophotometric instruments that obtain one or more measurements to extract this data for a single photosensor at one location on the object, the apparatus and methods of the present invention obtain this data using well-characterized narrow-band light sources with a monochrome sensor array that captures a mapping of spectrophotometric data for the full object.

In embodiments of the present invention, multiple signal values $S_{i(tooth)}$ are obtained, one for each of the N LED color light sources indexed i (i=1, 2, . . . , N). As equation (1) shows, in order to provide accurate and consistent measurement using $S_{i(tooth)}$, it is necessary to compensate for short-term changes in the device, such as from fluctuations in illuminant intensity and/or sensor response $D(\lambda)$. For this reason, as part of the imaging process, a reference target measurement $S_{i(ref)}$ is optionally obtained for use as calibration reference:

$$S_{i(ref)} = \int I_{LEDi}(\lambda)R_{ref}(\lambda)D(\lambda)d\lambda \quad (2)$$

wherein $R_{ref}$ is the reflectance of reference target 28. This value is obtained using image readings from reference target 28 (FIG. 3), which is positioned within the same captured field of view as the tooth in one embodiment. In an alternate embodiment, image readings from reference target 28 are obtained separately, such as at the beginning of an imaging session, for example.

Given values $S_{i(tooth)}$ and $S_{i(ref)}$, the more useful quantity for implementing the methods of the present invention is the corrected measurement value as given by:

$$\hat{S}_i = \frac{S_{i(tooth)}}{S_{i(ref)}} R_{ref}(\lambda) \quad (3)$$

wherein $R_{ref(\lambda)}$ is the known reflectance of the reference target 28 at the peak value of LEDi. The corrected measurement value $\hat{S}_i$ removes first-order sources of measurement variability and eliminates dependence on the scale of intensity or device response. From the corrected measurement value $\hat{S}_i$, the method of the present invention can be used to obtain visual color values to provide a highly accurate color mapping.

Each of the tristimulus color values X, Y, Z (hereafter represented by $X_q$ (q=1, 2, 3), where $X_1$=X, $X_2$=Y, and $X_3$=Z) for each pixel can be calculated from the tooth reflectance in the following way:

$$X_q = \int I(\lambda)R_{tooth}(\lambda)\bar{x}_q(\lambda)d\lambda \quad (4)$$

wherein the value of $\bar{x}_q(\lambda)$ is the corresponding visual color matching function of the standard observer, and $I(\lambda)$ is the spectral distribution of the light source under which the tooth is viewed.

Value $R_{tooth}(\lambda)$ is not directly measured by color measuring and mapping apparatus 40, but can be obtained using mixture coefficients that are derived from analysis of the sample set, such as using PCA, as described previously.

Spectral reflectance measurement results obtained from color measuring and mapping apparatus 40 can be used to calculate color tristimulus values for tooth under any lighting condition with known spectral energy distribution, according to equation (4). Applying this procedure to both teeth and shade-matching tab will yield two sets of tristimulus values from which the best match can be found. Alternatively, the tristimulus values can be converted to a different visual color space, such as the CIELAB or HSV color space, for finding the closest match between tooth and shade-matching tab.

The above approach has been described for a monochrome broadband sensor array. The same method can also be used if a conventional RGB color sensor array is used to provide a signal as each LED or other illumination source is energized. In the case of an RGB color sensor, the color channel with the highest signal level for a particular LED illumination can be used. If all three color channels of the sensor are used for each LED illumination, measured image data values will be obtained from a combination, such as a weighted sum, of the signals of the three color channels.

Using embodiments of the present invention, the task of obtaining a spectrophotometric color mapping of the tooth surface is simplified, and the cost of providing this data is significantly reduced over conventional alternatives. A result of applying the transformation matrix of the present invention is that only a few measurements are needed in order to obtain highly accurate color data. Measurements from illumination using only three or four LEDs has been found to be sufficient for color shade mapping in many intraoral imaging applications.

It is noted that the sequence of FIGS. 6A and 6B allow color mapping under any of a set of viewing illuminant conditions. The spectral reflectance mapping data that is collected can be used to calculate the color that is best matched with any source of viewing light, including incandescent light, fluorescent light, natural light or sunlight, or other source. Thus, for example, the spectral reflectance mapping data that is obtained in a dentist's office can be used to determine the best matched color for prosthesis viewed in natural light (sunlight), or for prosthesis viewed under stage lighting, such as for a model or performer, or for prosthesis viewed in fluorescent lighting in office environment, or other lighting conditions. This is an advantage of the method of the present invention over earlier RGB and colorimetric methods in which the color mapping and color match were constrained to the specific lighting conditions used in making the color measurement, which could be very different from the lighting condition that matters most to the patient.

The information obtained from the process of FIGS. 6A and 6B can be stored and used in a number of ways. The visual color values that are generated can be directly used to render the mapping for display, for example, or can be encoded in some way and stored in memory. Spectral reflectance values can be correlated with other tooth image data and provided to a dental laboratory or other facility for which accurate color characterization is useful.

It is noted that the method described in FIGS. 6A and 6B obtains multiple measurements for each pixel of the tooth image in one embodiment. This is potentially a sizable amount of data, but provides a full characterization of the spectral content of the tooth image, pixel by pixel. The data collected for the tooth image is non-metameric, thus eliminating the undesirable effects of illumination dependence that can compromise the color data when conventional colorimetric, RGB, or visually matched systems are employed for color mapping.

LEDs are advantaged as light sources for obtaining spectral reflectance data according to the present invention. In a preferred embodiment, the LED emits most of its light over a range of wavelengths that is less than about 40 nm. In one embodiment, the LED sources are substantially non-overlapping with respect to their respective wavelength bands, so that any leakage of light into adjacent bands is negligible. Other types of narrow band light sources could alternately be used to provide the needed illumination for reflectance measurements. Alternate types of light source include filtered light from a broadband light source, such as a lamp, for example. Four LEDs are shown in the example of FIG. 3. In general, at least three light sources of different wavelengths should be used.

Because the apparatus and methods of the present invention provide a mapping of spectral reflectance values, they promote accurate information about the true color of the tooth than is available when using conventional colorimetric or RGB-based measurement methods. Because spectral reflectance contains complete color information, independent of illuminant, the color data that are obtained are not subject to error due to metamerism. By using LEDs or other small sources, without the need for gratings or other devices, the apparatus of the present invention can be packaged in a compact fashion, at low cost. For example, color measuring and mapping apparatus 40 can be packaged as an intraoral camera.

Reference target 28 can be any suitable type of reference object, such as a patch, for providing a reference image for color imaging. A white or gray patch can be used, as well as some other patch having uniform spectral content. Target 28 can be separately imaged, or it can be positioned alongside the tooth, at approximately same distance from and within the imaging field of view of sensor array 44, such as in a fixed position, or may be pivoted into position, such as by energizing an actuator, for reference imaging as needed in the imaging cycle.

A number of computation functions are employed, such as for obtaining tristimulus values and for storing and displaying results, for example. It can be appreciated that these functions can be provided by a control logic processor 38 provided with or configured to interact with the color matching and mapping apparatus of the present invention. Stored instructions, for example, configure the processor logic circuitry to execute the color mapping data access, calculations, and output functions described above. Any of a number of types of control logic processor devices, such as a dedicated computer workstation, personal computer, or an embedded computing system that employs a dedicated data processing component (such as a digital signal processing component) could be used for computation functions. Control logic processing apparatus access an electronic memory for data storage and retrieval. An optional display device can also be provided for displaying color match and color mapping results.

The method and apparatus of the present invention employ a sensor array 34 as the detector in order to obtain a mapping with highly accurate color information. This component can include an arrangement of multiple CMOS or CCD sensors, typically assigned one per pixel. In one embodiment, a broadband monochrome sensor array is used. However, it is also possible to employ a sensor array that is configured for R, G, B color sensing, or configured for some other color space characteristics. Methods of obtaining spectral reflectance data in the present invention can be similarly applied to such devices, as has been discussed earlier. It is noted that pixel spacing can be varied for color matching, so that multiple sensor sites in sensor array 44 are grouped or clustered together, such as to obtain an averaged value, for example. Because the color measurement apparatus of the present invention uses an imaging sensor array, the same device that is used for conventional intra-oral color imaging can be configurable for both imaging and color measurement modes of operation. Referring to the schematic block diagram of FIG. 3, for example, color imaging can be performed by changing the pattern of illumination from the illumination apparatus 24, the resolution of the sensor array 34, and the color processing provided from control logic processor 38. A mode switch (not shown) or mode control command issued from an operator interface can be provided in order to set the operating mode of apparatus 40 for either conventional imaging or tooth color mapping as described herein.

Illumination apparatus 24 of the present invention employs multi-color LEDs in one embodiment. However, other light sources that can provide multiple color illumination could alternately be employed, including other types of solid-state light sources or more conventional lamps or lamps equipped with color filters.

Initial and periodic calibration of color measuring and mapping apparatus 40 are needed in order to compensate for component aging and drift, so that the profile of each LED in illumination source 12 can be maintained and regularly updated.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein

The invention claimed is:

1. An apparatus for obtaining a color mapping for a dental object, comprising:
   an illumination apparatus energizable to direct illumination of at least a first, a second, and a third wavelength band, one wavelength band at a time, toward the dental object;
   a monochrome image sensor array having broad spectral response over at least the first, second, and third wavelength bands, that is disposed with respect to an optical system and that is actuable to capture an image of the dental object at each illumination wavelength band to form a set of images of the dental object;

a reference target that is disposed in the object field of the optical system and substantially in focus with respect to the image sensor array; and a control logic processor operatively connected with the illumination apparatus and monochrome image sensor array and responsive to stored instructions to energize the illumination apparatus to sequentially provide the at least first, second, and third wavelength bands and further responsive to stored instructions to capture and store an image at each wavelength band, to calculate image data values for each pixel, and to generate and store a color mapping according to a sample set of spectral reflectance data and according to measured image values from the sample set.

2. The apparatus of claim 1 wherein the apparatus is in the form of an intraoral camera.

3. The apparatus of claim 1 wherein the control logic processor is adapted to:

generate a set of tristimulus values from the set of spectral reflectance data;

obtain a set of image sample measurements by directing illumination toward each tooth over the at least first, second, and third wavelength bands, one wavelength band at a time, wherein the set of image sample measurements are obtained at the same locations on the teeth as the set of spectral reflectance data;

generate a plurality of mixture coefficients by applying principal component analysis to the set of image sample measurements;

form a transformation matrix using a least squares fit between the plurality of mixture coefficients and the set of tristimulus values; and apply the transformation matrix to form the color mapping.

4. The apparatus of claim 1 wherein the control logic processor is adapted to:

generate a set of visual color values from the set of spectral reflectance data;

obtain a set of image sample measurements by directing illumination toward each tooth over the at least first, second, and third wavelength bands, one wavelength band at a time, wherein the set of image sample measurements are obtained at the same locations on the teeth as the set of spectral reflectance data;

form a transformation matrix using a least squares fit between the image sample measurements and the set of visual color values; and apply the transformation matrix to form the color mapping.

* * * * *

UNITED STATES PATENT AND TRADEMARK OFFICE
CERTIFICATE OF CORRECTION

PATENT NO.       : 8,768,025 B2                                    Page 1 of 1
APPLICATION NO.  : 14/040776
DATED            : July 1, 2014
INVENTOR(S)      : Wong et al.

It is certified that error appears in the above-identified patent and that said Letters Patent is hereby corrected as shown below:

In the specification,

Column 10, Line 10    Please replace the word "e" with the word --*e*--
Column 11, Line 18    Please replace the word "l$_2$" with the word --$\ell_2$--

Signed and Sealed this
Twenty-eighth Day of April, 2015

Michelle K. Lee
*Director of the United States Patent and Trademark Office*